United States Patent
Abraham et al.

(10) Patent No.: US 9,266,898 B2
(45) Date of Patent: Feb. 23, 2016

(54) REACTION PRODUCT FROM THE CO-DEHYDRATION OF A SUGAR ALCOHOL AND A POLYOL

(75) Inventors: Timothy Walter Abraham, Minnetonka, MN (US); Donald Michael Ference, Woolwich Township, NJ (US); Wei Zhang, Eden Prairie, MN (US)

(73) Assignee: Cargill, Incorporated, Wayzata, MN (US)

( * ) Notice: Subject to any disclaimer, the term of this patent is extended or adjusted under 35 U.S.C. 154(b) by 172 days.

(21) Appl. No.: 13/994,499

(22) PCT Filed: Dec. 16, 2011

(86) PCT No.: PCT/US2011/065438
§ 371 (c)(1),
(2), (4) Date: Jul. 18, 2013

(87) PCT Pub. No.: WO2012/083146
PCT Pub. Date: Jun. 21, 2012

(65) Prior Publication Data
US 2013/0296451 A1     Nov. 7, 2013

Related U.S. Application Data

(60) Provisional application No. 61/424,379, filed on Dec. 17, 2010.

(51) Int. Cl.
| | | |
|---|---|---|
| C07D 493/04 | (2006.01) |
| C08G 18/32 | (2006.01) |
| C08G 18/48 | (2006.01) |
| C08G 18/40 | (2006.01) |
| C08G 101/00 | (2006.01) |

(52) U.S. Cl.
CPC .......... *C07D 493/04* (2013.01); *C08G 18/3218* (2013.01); *C08G 18/4018* (2013.01); *C08G 18/4883* (2013.01); *C08G 2101/0025* (2013.01); *C08G 2101/0083* (2013.01); *C08G 2105/02* (2013.01)

(58) Field of Classification Search
None
See application file for complete search history.

(56) References Cited

U.S. PATENT DOCUMENTS

| | | | |
|---|---|---|---|
| 3,454,603 A | | 7/1969 | Hartmann |
| 3,586,715 A | * | 6/1971 | Smeets .......................... 562/595 |
| 4,076,633 A | | 2/1978 | Edwards et al. |
| 4,408,061 A | | 10/1983 | Salzburg et al. |
| 4,443,563 A | | 4/1984 | Dirlikov et al. |
| 4,564,645 A | | 1/1986 | Salzburg et al. |
| 5,837,669 A | | 11/1998 | Petit et al. |
| 6,013,812 A | | 1/2000 | Haas et al. |
| 6,407,266 B2 | | 6/2002 | Bhatia |
| 6,689,892 B2 | | 2/2004 | Andrews et al. |
| 6,849,748 B2 | | 2/2005 | Moore et al. |
| 7,615,652 B2 | | 11/2009 | Holladay et al. |
| 2002/0002291 A1 | * | 1/2002 | Bhatia ........................... 549/465 |
| 2004/0092703 A1 | | 5/2004 | Germroth et al. |
| 2005/0267278 A1 | * | 12/2005 | Nichols et al. .................. 528/44 |
| 2007/0173651 A1 | * | 7/2007 | Holladay et al. ............. 549/416 |
| 2009/0171060 A1 | | 7/2009 | Gerkin et al. |

FOREIGN PATENT DOCUMENTS

| | | |
|---|---|---|
| WO | 2012/083149 A1 | 6/2012 |
| WO | 2013/089792 A1 | 6/2013 |

OTHER PUBLICATIONS

American Diabetes Association, Sugar Alcohols, 1995.*

* cited by examiner

*Primary Examiner* — Randy Gulakowski
*Assistant Examiner* — Jeffrey Washville

(57) ABSTRACT

A reaction product of the co-dehydration of a sugar alcohol and a reactant polyol having a number average hydroxyl functionality less than 4.0 is disclosed. In some aspects the sugar alcohol comprises mannitol, sorbitol, xylitol, erythritol, or mixtures thereof. In some preferred aspects the sugar alcohol comprises sorbitol. In some aspects the reactant polyol has an average molecular weight of from 40 to 500 Daltons. In some aspects, the reaction product may be suitable for the manufacture of polyisocyanurate foam. In some aspects the reaction product may be mixed with diluent polyols, such as diols, glycols, ethylene glycol, diethylene glycol, dipropylene glycol, propylene glycol, polyethylene glycol, polypropylene glycol and mixtures thereof.

22 Claims, No Drawings

REACTION PRODUCT FROM THE CO-DEHYDRATION OF A SUGAR ALCOHOL AND A POLYOL

CROSS REFERENCE TO RELATED APPLICATIONS

This application is a section 371 national-stage phase of International Application No. PCT/US2011/065438, filed 16 Dec. 2011, titled "REACTION PRODUCT FROM THE CO-DEHYDRATION OF A SUGAR ALCOHOL AND A POLYOL" which claims priority to U.S. Application Ser. No. 61/424,379, filed 17 Dec. 2010, titled "REACTION PRODUCT FROM THE CO-DEHYDRATION OF A SUGAR ALCOHOL AND A POLYOL" which is hereby incorporated by reference in its entirety

FIELD

This invention relates to polyols made from the reaction product resulting from the acid-catalyzed co-dehydration of a sugar alcohol and a reactant polyol. In some particular embodiments, the reactant polyol has an average of from two to three hydroxyl groups.

BACKGROUND

Sugar alcohols, such as sorbitol, have been dehydrated in order to produce isosorbide, which is a 6-carbon and heteroatom containing bicyclic ring compound with fused rings. It is formed by the removal of two water molecules by dehydration of sorbitol. During the first dehydration step the sorbitol is converted to sorbitan; and during the second dehydration step the sorbitan is converted to isosorbide. The final reaction mixture resulting from the dehydration typically contains greater than 70 percent isosorbide, which is typically purified to at least 99% through distillation to obtain isosorbide suitable for the manufacture of pharmaceuticals and use in polymer applications. Purified isosorbide is a crystalline solid having a melting point of about 61 to 63° C. The purified isosorbide typically is distributed in solid crystalline form.

SUMMARY

In a first embodiment, the invention is a composition comprising the reaction product of the co-dehydration of a sugar alcohol and a reactant polyol having a number average hydroxyl functionality less than 4.0.

In a second embodiment, the invention is a composition comprising a reaction product of the acid catalyzed co-dehydration of a sugar alcohol and a polyol, wherein the reaction product comprises from about 25 to about 65 weight percent isosorbide, and at least 2 percent oligomers.

In a third embodiment, the invention is a composition suitable for use in the manufacture of a rigid polyurethane foam, the composition comprising:
(a) a diluent polyol having at least two hydroxyl groups; and
(b) the reaction product of any of the above first and second embodiments, wherein, a weight ratio of the diluent polyol to reaction product is less than about 3:7.

In a fourth embodiment, the invention is a composition comprising a reaction product of the acid catalyzed co-dehydration of sorbitol and from 5 to 15 percent by weight glycerol, wherein the reaction product comprises from about 40 to about 50 weight percent isosorbide, at least 5 percent by weight oligomers, less than 1.5 percent by weight water, and less than 8 percent by weight free glycerol and exhibits a hydroxyl number of from about 800 to 1100 mg KOH/gram and a viscosity at 25° C. of from about 6 to 40 Pa·s.

In a fifth embodiment, the invention is a composition suitable for use in the manufacture of a rigid polyurethane foam, the composition comprising:
(a) a diluent polyol having at least two hydroxyl groups; and
(b) the reaction product of any of the above embodiments, wherein, a weight ratio of the diluent polyol to reaction product is less than about 2:8 and wherein the composition exhibits a viscosity at 25° C. of less than 15 Pa·s.

In a sixth embodiment, the invention is a rigid foam made from the reaction of any of the compositions of the above embodiments with a polyisocyanate.

In a seventh embodiment, the invention is a process for the production of a liquid polyol that will remain a liquid at room temperature, the process comprising:
(a) reacting sorbitol with a reactant polyol having an number average functionality (Fn) of from two to three with from about 0.01 percent by weight to about 5 percent by weight acid (preferably less than 1 percent by weight, and further more preferably less than 0.5 percent by weight) at a temperature of from about 100° C. to about 195° C. (preferably from 130° C. to 180° C.);
(b) removing water from the reaction mixture; and
(c) continuing the reaction to obtain a liquid polyol comprising from about 25 to about 65 percent by weight isosorbide (preferably from about 30 to 55 percent by weight isosorbide), at least 2 percent by weight oligomers (preferably at least 3 percent by weight), and having a viscosity of less than about 60 Pa·s at 25° C. (preferably less than 40 Pa·s at 25° C.) and a hydroxyl number of from about 500 to about 1200 mg KOH/gram liquid polyol.

DETAILED DESCRIPTION

Terms and Definitions:

As used herein "polyol" refers to a molecule having an average of greater than 1.0 hydroxyl group per molecule (i.e. a number average hydroxyl functionality (Fn) of greater than 1.0). A polyol may also include functionality other than hydroxyl groups.

"Hydroxyl number" (OH#) is a measure of the hydroxyl (—OH) groups present in a polyol. It is reported in units of mg KOH/gram polyol and is measured according to the procedure of ASTM E1899-02; with the modification that 5 ml of tetrahydrofuran is used to initially dissolve the reaction product instead of acetonitrile.

"Number average molecular weight" (Mn) is determined according to procedure known to one of skill in the art; and is reported in units of Daltons.

"Fn" is the number average hydroxyl functionality expressed in number of hydroxyl groups per polyol molecule. Fn is calculated using the equation:

$$Fn = (OH\#/56)*(Mn/100)$$

"Oligomers" for purposes of this invention refers to molecules that are made from the reaction of at least: (1) one of the monomers with another monomer or another molecule that is derived from one of the monomers; and (2) one of the monomers with itself. For purposes of this definition the sugar alcohol would be a monomer and the reactant polyol would be a monomer. Also, for purposes of this invention examples of a molecule derived from a monomer would include sorbitan and isosorbide, which are both derived from sorbitol directly or indirectly. For clarification, the molecule that results from linking a sorbitan molecule with a glycerol through an ether link would be a oligomer, as would the molecule that results from linking a glycerol molecule with another glycerol molecule through an ether link. The molecule that results from the linking of two isosorbide molecules to form a dimer would also be considered an oligomer for purposes of this invention. In general the oligomers are compounds containing one or more intermolecular ether linkages formed during the codehydration process. The ethers for example, can be formed between sorbitol and glycerol, sorbitan and glycerol, sorbitan and sorbitan, sorbitan and isosorbide, an isosorbide with another isosorbide, glycerol with isosorbide, glycerol with another glycerol, etc.

"Sugar Alcohol" refers to any of the acyclic linear polyhydric alcohols derived from carbohydrates. Typically sugar alcohols may be obtained by reducing the aldehyde group of the first carbon atom of a sugar monosaccharide to a primary alcohol.

"Acid Value" (AV) is determined according to the standard IUPAC method 2.201, with the modification that distilled water is used as the solvent. Acid Value (AV) is reported in units of mg KOH/gram of material.

"Isocyanate index" as used herein, refers to a measure of the stoichiometric balance between the equivalents of isocyanate groups used, to the equivalents of active hydrogens present from polyols, water, and other reactive components. An isocyanate index of 100 means enough isocyanate groups are provided to be able to theoretically react with all the active hydrogen groups present in the formulation. An isocyanate index of 200 means there is two (2) times more isocyanate groups than needed to react with all the active hydrogen groups present in the formulation.

"Polyisocyanurate (FIR) foam," for the purpose of this invention, refers to a polyurethane foam that results from the reaction of methylenediphenyldiisocyanate (MDI) and a polyol with an isocyanate index above 150. The catalysts utilized typically are different from commonly used polyurethane foam catalysts. The catalysts utilized for PIR foams promote a trimerization reaction to form isocyanurates. Examples of these catalysts typically are metal salts (preferably Group I metal salts, such as potassium acetate and potassium octoate). Examples of other PIR catalysts are amine-based isocyanate trimerization catalysts, for example DABCO TMR available from Air Products. The PIR foams typically are stiffer than polyurethane foams made with a lower isocyanate index. The FIR foams typically are more chemically and thermally stable than non PIR polyurethane foams. The isocyanate index utilized for PIR foams typically is less than 500. Preferably the isocyanate index utilized to make PIR foams is from 200 to 300. The density of PIR foams can be adjusted depending on the overall physical properties desired in the foams.

"Viscosity" is measured using a AR 2000 Rheometer available from TA Instruments Inc. Measurement conditions are: cone and plate measuring system, gap distance of 150 μm, plate diameter of 25 mm, cone angle of 5 degree and temperature of 25° C.

GPC Analysis:

Gel permeation chromatograph ("GPC") analysis was done on a Waters system using Water 510 pumps and a series of columns of Phenogel 5-50A 300×7.8 mm, Phenogel 5-100A 300×7.8 mm, Phenogel 5-10$^3$A 300×7.8 mm, Phenogel 5-10$^4$A 300×7.8 mm, Phenogel 5-Linear/Mixed, 50×7.8 mm. (Phenogel columns from Phenomenex, Torrance, Calif.). Tetrahydrofuran (THF) at a flow rate of 1 mL/min was used as a mobile phase. The samples were injected as 1.0% (w/v) solutions in the mobile phase using manual 200 μL injector (Rheodyne, Rohnert Park, Calif.). The measurements were carried out at room temperature (25°)

The chromatogram from GPC showed 3 major peaks with retention times of 38.0-38.2 minute, 38.8-38.9 minute and 40.0-40.1 minute The peaks at 38.9-39.0 minute and 40.1-40.2 minute were assigned to sorbitan and isosorbide respectively, based on the analysis of pure compounds. The peak at 38.0 minute was assigned to higher molecular weight oligomers due to the lower retention time. One of skill in the art will understand that while the position (time) of the peaks may shift from run to run, that the relative position of the various peaks for the molecules of interest with respect to one another will remain the same. The retention times in the chromatograms, corresponding to the different compounds, may change slightly from sample to sample, but their relative positions do not change.

"Water Content is measured according to the method of ASTM E1064-08.

"k-factor" is measured in accordance with the procedures of ASTM-C518-04. K-factor is reported in units of watts per kelvin-meter (W/K×m).

"Compressive Strength" is measured according to the procedures of ASTM-D1621-00.

"Density" of the foams is measured according to the procedures of ASTM-D1622-98.

The "Sugar Alcohol":

Sugar alcohols that can be utilized in the invention include C4 to C6 sugar alcohols. Preferably, C6 sugar alcohols, such as mannitol and sorbitol are used. Due to its wide availability and ability to form a bicyclic ring structure upon dehydration, sorbitol is the more preferred sugar alcohol to utilize. Sorbitol $(C_6H_8(OH)_6)$ is a six carbon sugar alcohol that is typically made by the hydrogenation of glucose. Sorbitol can also be obtained in a complex mixture by the hydrogenation of a composition obtained from the hydrolysis of sucrose. For example, unrefined sugar from sugar cane and/or sugar beets can be hydrolyzed and then hydrogenated to obtain a composition typically containing from about 40 to 80 percent by weight sorbitol (the remainder typically comprising from 20 to 60 percent by weight mannitol and other materials). Similarly high fructose corn syrup, obtained by the enzymatic conversion of glucose can be hydrogenated to a composition comprising sorbitol and mannitol. Other sugar alcohols that can be utilized include xylitol and erythritol, which can be obtained from the fermentation of carbon sources.

The single dehydration reaction of sorbitol typically produces sorbitan. Isosorbide can be obtained from a double dehydration reaction of a sorbitol molecule. Isosorbide is a bicyclic fused ring molecule having the chemical formula: $C_6H_{10}O_4$.

Mannitol $(C_6H_8(OH)_6)$ can be produced by biotechnology routes, and it can be synthesized along with sorbitol by the hydrogenation of fructose. As discussed above, mannitol is also obtained by the hydrolysis and hydrogenation of sucrose or compositions containing sucrose. The single dehydration reaction of mannitol typically produces mannitan. Isomannide can be obtained from a double dehydration reaction of a mannitol molecule.

The Reactant Polyol:

In one embodiment, the polyol utilized in the co-dehydration reaction with sorbitol typically has less than 4 hydroxyl groups per molecule (Fn<4). Preferably, in this embodiment the polyol has 2 to 3 hydroxyl groups per molecule (Fn=2 to 3). The polyol preferably is a liquid at room temperature (25° C.) and typically has a molecular weight of from 40 to 500

Daltons, preferably 50 to 300 Daltons, and more preferably from 60 to 200 Daltons. Examples of polyols that can be utilized in the invention include glycols, ethylene glycol, propylene glycol, polyethylene glycol, 1,3-propanediol, 1,4-butanediol, polypropylene glycol, glycerol, glycerol esters, 1,4-dihydroxycyclohexane, diethylene glycol, poly(1,3-propanediol), poly(1,4-butanediol), and dipropylene glycol, and mixtures thereof. The polyols may contain heteroatoms other than oxygen. Due to its ready availability, relatively low molecular weight and three hydroxyl groups (i.e. Fn=3), glycerol preferably is utilized. The polyol is typically selected so that the boiling point of the polyol under the reaction conditions (i.e the existing temperature and pressure experienced by the reactive mixture) is typically at least 30° C., preferably at least 50° C., and more preferably at least 100° C. above the reaction temperature utilized for the dehydration reaction. For example, if glycerol is the polyol utilized, the reaction temperature typically is from 100° C. to 160° C., the pressure is about 760 mm Hg, and the boiling point of glycerol is 290° C. at this pressure.

Co-Dehydration Reaction:

The co-dehydration reaction may be catalyzed or uncatalyzed. Both acid and base catalysts may be utilized. The reaction preferably is catalyzed with an acid, which can be an inorganic or organic acid. The acid catalyst may also be a homogeneous or heterogeneous catalyst. The latter includes a homogeneous catalyst (eg. sulfuric acid) immobilized on a solid support (eg. silica). Examples of inorganic acid catalysts that may be utilized include acids, such as sulfonic, sulfuric, hydrochloric, hydrofluoroboric, phosphoric, and hypophosphorous acids. Examples of organic acid catalysts that can be utilized include p-toluenesulfonic acid and trifluoromethanesulfonic acid. Examples of base catalysts that may be utilized include sodium hydroxide, potassium hydroxide and sodium carbonate. When an acid catalyst is utilized, the catalyst typically comprises from 0.001 to 5 weight percent of the reactive mixture, preferably from about 0.01 to 2.0 percent by weight of the reactive mixture, and more preferably from 0.03 to 1.0 percent by weight of the reactive mixture and sometimes from 0.05 to 0.5 percent by weight of the reactive mixture.

The reaction typically is carried out at temperatures from 100° C. to 195° C., from 120° C. to 190° C., or from 130° C. to 180° C., for example, 130° C. to 165° C. The pressure of the reaction typically is initially at atmospheric pressure (i.e. for the first few hours of reaction) and then is lowered from a slight vacuum to a pressure of 150 to 250 torr, preferably less than 200 torr, and sometimes from 30 to 100 torr. The weight ratio of reactant polyol to sugar alcohol typically is from 1:99 to 40:60, from 5:95 to 30:70, preferably from 5:95 to 25:75, and more preferably from 7:93 to 20:80. Water is removed during the reaction in order to promote/enhance the formation of the reaction product. As described above, a slight vacuum may be applied to the reactor in order to enhance the removal of water. The reaction typically is carried out until the desired isosorbide content is obtained, then the reaction typically is stopped. Methods known to one of skill in the art can be utilized to stop the reaction. For example, the temperature can be reduced below the reaction temperature. Alternatively, an additive can be introduced that stops the reaction. For example, if a catalyst is used, an agent can be introduced to stop or greatly reduce the reaction. For example, if an acid catalyst is utilized, an inorganic base compound (such as, for example, potassium hydroxide and/or sodium hydroxide) and/or an organic base compound (such as, for example, triethanolamine or diethanolamine) can be introduced to neutralize the acid catalyst. Likewise, if a base catalyst is utilized, an acid compound can be introduced to neutralize the base catalyst. Also, the additive can be utilized in connection with lowering the temperature, in order to obtain the desired concentration of isosorbide. In an alternate aspect, no additive is utilized, but the heat is removed from the reaction (and/or cooling is applied) to obtain the desired final isosorbide content in the reaction product.

The desired level of isosorbide typically is from 25 to 65 percent by weight, preferably from 30 to 55 percent by weight, more preferably from 35 to 50 percent by weight, and in some instances 40 to 45 percent by weight of the reaction product. The inventors have found that the viscosity of the reaction product decreases as the weight percent of the isosorbide increases, but eventually the viscosity starts to increase as the amount of by-products, such as oligomers, increase. The inventors have also surprisingly found that if the weight percent of the isosorbide is maintained below a certain level, crystallization within the reaction product when it is cooled to room temperature (25° C.) can be prevented or minimized. This provides a composition that can be readily handled for a variety of end-use applications. The amount of isosorbide is measured using liquid chromatography as further described below.

The amount of isosorbide present during the reaction does not need to be measured directly. Instead, the amount of water removed may be used to estimate how far the reaction has progressed. By carrying out several test manufacturing runs, a correlation can be developed that relates the amount of isosorbide present in the reaction product to the amount of water removed from the reactor. Also, the amount of weight loss from the reactor can be monitored in order to determine the degree of isosorbide formation and use this information to determine when to stop the reaction. Also, once appropriate experience has been gained in the manufacture of the reaction product; knowledge of the reactants present, the temperatures and pressures utilized and the time of reaction may be sufficient to determine when to stop the reaction and obtain the desired isosorbide content in the reaction product.

The Reaction Product:

The reaction product typically has a viscosity of 60 Pa·s or less at 25° C., preferably 40 Pa·s or less, and more preferably 30 Pa·s or less at 25° C.

As discussed earlier, the reaction product typically has from about 25 to 65 percent by weight isosorbide as determined by liquid chromatography analysis, preferably from 30 to 55 percent by weight, and more preferably from 35 to 50 percent by weight. Preferably, the reaction product is substantially free of visible crystals at room temperature. By substantially free of visible crystals it is meant that the solution is substantially a single phase, homogeneous liquid, which lacks visible haze or turbidity when visually inspected. Additionally, if substantial crystals are present in the reaction product, the overall liquid may appear to be crystal free, but the surface of the reaction product will often appear to be rough or non-smooth. Typically, the reaction product is substantially free of crystals visible to the naked eye for at least 8 hours after the reaction is complete, and the reaction product has been cooled to 25° C. Preferably, the reaction product is substantially free of crystals for 10, 20, 30, 60, 90 days at 25° C. after being produced. To further reduce crystallization, a diluent, as described more fully below may be added to the reaction product.

The reaction product typically has at least 2 percent by weight oligomers, preferably at least 3 percent by weight oligomers, and may have at least 5, 7, 8, 9, and sometimes at least 10, for example, at least 15 percent by weight oligomers based on the weight of the reaction product. While not intending to be bound by theory, it is believed that the high levels of oligomers, especially co-dehydrated products from different monomers, may enhance the tendency of the reaction product to remain a liquid at room temperature (25° C.).

The reaction product typically has a hydroxyl number of 1200 mg KOH/gram or less, preferably less than 1100 mg KOH/gram, and in some instances less than 1000 mg KOH/gram. In some aspects, the reaction product has a hydroxyl number from 800 to 1100 mg KOH/gram, sometimes from 850 to 1050 mg KOH/gram.

The reaction product can be utilized neat or a diluent (as described below) may be added to the reaction product. Examples of diluents that typically are utilized include diethylene glycol, dipropylene glycol, polyethylene glycol, glycerol, polyglycerol, polypropylene glycol, ethylene glycol, propylene glycol, 1,3-propanediol, poly(1,3-propanediol), 1,4-butanediol, and poly(1,4-butanediol). The diluent may include heteroatoms other than oxygen. Typically, the diluents utilized have a number average hydroxyl functionality (Fn) of less than 4, and preferably have a number average hydroxyl functionality of from 2 to 3. Typically, the diluents are liquid at 25° C., and have a viscosity less than 5 Pa·s at 25° C., preferably less than Pa·s, and more preferably less than 0.2 Pa·s at 25° C. Water may also be added to the reaction product, either alone or together with another diluent. If the reaction product is to be utilized for polyisocyanurate foams as described below, the water typically is at levels of 2% by weight or less, preferably 1.5% by weight or less, and sometimes 1.0% by weight or less of the composition containing the reaction product and any diluent present (including water). After the diluents have been added, the viscosity typically is 30 Pa·s or less at 25° C., preferably 20 Pa·s or less, more preferably 15 Pa·s or less at 25° C., and most preferably 10 Pa·s or less at 25° C.

When particularly low viscosity reaction products are desirable (for example a viscosity of 10 Pa·s or less at 25° C., and in some instance less than 8 Pa·s, 6 Pa·s, 4 Pa·s at 25° C.), the reaction product may be alkoxylated using, for example, ethylene oxide, propylene oxide, butylene oxide, or mixtures thereof in accordance with methods known to one of skill in the art to further lower the viscosity of the reaction product. During such alkoxylation, typically 1 percent by weight to 50 percent by weight of alkylene oxides based on the weight of the reaction product (for example 5 percent by weight to 30 percent by weight, and where high bio-based content is desirable in the final reaction product from 5 percent by weight to 10 percent by weight) are used in the reaction. The hydroxyl number of the resulting polyols typically will be from 200 to 800 mg KOH/gram, for example from 210 to 400 mg KOH/gram and preferably from 220 to 250 mg KOH/gram, and when the alkoxy groups make up from 5 to 10 percent by weight of the final reaction product, the hydroxyl number will typically be from 750 to 1000 mg KOH/gram.

After a diluent has been added to the reaction product, the resulting material typically has a hydroxyl number of 1300 mg KOH/gram or less, preferably less than 1250 mg KOH/gram, and more preferably less than 1200 mg KOH/gram, and in some instances less than 1000 mg KOH/gram. The amount of diluent to be added may vary depending on whether unreacted polyol is present in the reaction product. For example, the inventors have found that when 5-10 percent by weight glycerol is reacted with the sorbitol, 3 to 7 percent by weight glycerol may remain after the reaction is complete. This remaining glycerol will act as a diluent for the isosorbide and therefore reduce the viscosity of the reaction product and therefore reduce the amount, if any, of additional diluents (such as glycerol) to be added to obtain a given viscosity.

Uses for the Co-Dehydrated Reaction Product

Isocyanurate Foam Applications:

The reaction products can be utilized in a variety of end-use applications. For example, the reaction product can be used in the manufacture of polyesters and polyurethanes. For polyurethanes, the reaction products can be utilized in foam applications and in coatings, adhesives, sealants, and elastomers (CASE) type applications. In one particular preferred embodiment, the reaction product is utilized in the manufacture of rigid polyurethane foams. In another particular preferred embodiment, the reaction product is utilized in the production of polyisocyanurate foams.

EXAMPLES

Materials Utilized:

"C* Sorbidex C-16106" a 70% by weight aqueous solution of 98% by weight purity sorbitol available from Cargill, Incorporated.

"Sorbitol Solution #177010" is a 70% by weight aqueous solution of sorbitol available from Archer Daniels Midland Company.

"p-Toluenesulfonic acid" (99% pure) a dry granular solid available from Aldrich Chemical. In the tables referred to as PTA.

"Terate®4020" an aromatic polyester polyol available from Invista. In the tables referred to as Terate-4020.

"Dabco® DC-197" a silicone surfactant available from Air Products and Chemicals. In the table referred to as DC-197.

"AntiBlaze® TMCP" a chlorinated phosphate ester fire retardant available from Albemarle™ Corporation. In the tables referred to as AB-TMCP.

"POLYCAT® 5" a blowing amine catalyst available from Air Products and Chemicals.

"DABCO TMR-3®" a trimerization catalyst available from Air Products and Chemicals. In the tables referred to as TMR-3.

"TR-52" a back end cure catalyst available from Pelron Corporation.

"n-Pentane" a hydrocarbon blowing agent available from ConocoPhillips Company.

"Mondur E-489" a diphenylmethanediisocyanate (MDI) available from Bayer Material Science LLC.

"Diethylene glycol" available from Huntsman International LLC. In the tables referred to as DEG.

"Sulfuric acid", 95-98%, a product available from EMD Chemicals Inc. In the table referred to as SFA.

Glycerin, USP/Kosher Grade, available from Cargill

For the Tables:
 ISB=Isosorbide
 SBT=Sorbitol
 GLY=Glycerin
 ERT=Erythritol
 CAT=Catalyst
 RX Temp=Reaction Temperature
 VISC=Viscosity @25° C.
 SBTN=Sorbitan
 PS=Partially Solid
 L=Liquid
 S=Solid

EXPERIMENTAL PROCEDURE FOR HIGH PRESSURE (OR PERFORMANCE) LIQUID CHROMATOGRAPHY (HLPC) ANALYSES OF SAMPLES

Equipment:
  Waters® 2695 liquid chromatograph or equivalent
  Waters® Empower™ software
  Waters® 2414 refractive index detector
  Waters® temperature control module
  BioRad® HPX-87 C ion exchange column (pn 125-0095)
  Syringe filters, Acrodisc CR 25 0.2 micro-m (pn 4225T)

Instrument Conditions:
  Mobile phase: UHP water @0.7 mL/minute
  Detector: Differential refractive index, sensitivity=4, 30° C. cell temp
  Column heater: 85° C.
  Injection volume: 20 microliters Sample Preparation In order to plot standard curves, a series of six standard solutions containing isosorbide, sorbitol and glycerol are prepared in ultra high pure (UHP) water. The six standard solutions contain 8000, 4000, 2000, 1000, 500, and 200 ppm of isosorbide, and 100 ppm, 50 ppm, 25 ppm, 12.5 ppm, 6.25 ppm and 2.5 ppm each of sorbitol and glycerol respectively. The individual solutions were injected into the chromatograph, and standard curves (i.e. concentrations for a given response) were generated for isosorbide, sorbitol and glycerol based on the area under the peaks as determined from the chromatagrams. The standard curve for isosorbide was used to estimate the sorbitan concentration, since a highly pure sorbitan sample was unavailable.

For each experimental sample, approximately 0.15 grams is weighed into a 10 mL volumetric flask, the weight recorded, diluted to 10 mL volume with UHF water, and mixed well. The samples are filtered through a 0.2 micron filter into vials, and 20 microliters of each filtered sample is injected into the chromatograph. The chromatograms obtained for each sample are evaluated against the standard curves. Utilizing the retention time of the peaks, and the area under each peak, the quantity of isosorbide, sorbitan, sorbitol, and glycerol was determined. The oligomers present in each experimental sample was determined based on the retention times and response of the high molecular weight compounds shown in the chromatograms, and a percentage reported for these oligomers based on the area under the high molecular weight component peaks relative to the area under all the peaks in the chromatogram.

Example 1

Co-Dehydration of Sorbitol with 10% by Weight Glycerol at 160° C. with 0.13-0.15% by Weight Sulfuric Acid 385.71 grams of C* Sorbidex C-16106 is charged into a 1000 ml three neck round bottomed flask, equipped with a mechanical stirrer, heating mantle, temperature controller, nitrogen sparge and water collector. Heat is applied to the flask while agitating the content of the flask and sparging nitrogen through the contents. Water is removed from the flask once the material in the flask reaches a temperature of from 110 to 120° C. The temperature is maintained at 130-140° C. for around 30 minutes until water collection slowed significantly. A medium vacuum of about 200-300 mbar is applied, and the temperature is maintained from 130-140° C. for another 20 minutes until 99% of the water that was in the sorbitol solution is stripped out. 0.80 to 0.84 grams of a 1:1 water: sulfuric acid mixture along with 30 grams of glycerol are charged to the flask. A distillation column is inserted between the water collector and the flask. The flask is maintained at 160° C. with no vacuum applied with agitation and a nitrogen sparge for one hour. A vacuum of 200 mbar is applied. The reaction is continued at 160° C. with agitation and a nitrogen sparge, until the reaction has continued to a point where a reaction product having the isosorbide levels indicated in Table 1 will be obtained. For the reactions of Example 1, the extent of the reaction is measured by measuring the weight loss from the flask. Once the reaction has reached the extent desired, the flask is cooled to below 100° C. and then the resulting reaction product is transferred to a glass container and stored at room temperature (25° C.). The resulting reaction products have the physical and chemical properties indicated in Table 1. The entire reaction typically takes from between 1 to 3 hours at the given reaction temperatures and pressures, depending on the desired final isosorbide weight percent in the reaction product.

Initially, all the reaction products described in Table 1 are liquid upon cooling to room temperature.

TABLE 1

| Sample No. | HPLC | | | | GPC | OH# | AV | Difference | H2O |
|---|---|---|---|---|---|---|---|---|---|
| | ISB wt % | SBTN wt % | GLY wt % | Oligomers wt % | *ISB wt % | (mg KOH/g) | (mg KOH/g) | between HPLC and GPC on ISB | wt % |
| 1-1 | 53.49 | 17.47 | 5.69 | ≥8.33 | 65.97 | 935 | 1.48 | 12.48 | ** |
| 1-2 | 47.13 | 25.96 | 5.86 | ≥9.04 | 58.72 | 1010 | 1.76 | 11.59 | ** |
| 1-3 | 39.25 | 35.13 | 6.05 | ≥7.39 | 52.65 | 1014 | 1.48 | 13.4 | ** |
| 1-4 | 30.77 | 45.16 | 6.23 | ≥6.35 | 43.51 | 1049 | 1.70 | 12.74 | ** |
| 2-1 | 44.98 | 27.84 | 5.98 | ≥7.63 | 57.59 | 1002 | 1.5 | 12.61 | 1.23 |

*This is the amount of isosorbide indicated by GPC with no correction factor applied
** these samples had less than 1 wt % water.

Example 2

Co-Dehydration of Sorbitol with 10% by Weight Glycerol at 160° C. with 0.13-0.15% by Weight Sulfuric Acid in a Larger Scale Reactor Reactor Design:
  The reactor consists of a 190 liter 304 Stainless Steel pressure vessel, jacketed for cooling with chilled water and an internal coil for heating with hot oil. The reactor contains a mechanical agitator driven by a 1 horsepower air powered motor for continuous agitation of the reactive mixture. The overhead condenser is a shell and tube heat exchanger with cooling water on the shell side and located in between the vacuum pump and the reactor. The overhead condenser condenses vapors into liquid, which then gravity feeds into a 23 liter condensate receiver. When desired, vacuum is pulled on the reactor, through the overhead condenser by the vacuum pump. A dry ice trap is installed between the outlet of the overhead condenser and the inlet of the vacuum pump to condense any vapors not condensed at the cooling water temperature. The resulting reaction product in the reactor is unloaded through a Stainless Steel Filter with a 50 micron Polyester Filter Element.

Stripping Water from the Sorbitol:

The reactor is charged with 204.5 kgs of Sorbitol Solution #177010.

The agitator is started and the speed set to approximately 2500 rpm.

The oil heater is set to maintain the reactor temperature at 130° C.

The vacuum pump is started and the vent valve to the vacuum pump is slowly closed gradually establishing a vacuum of ~150 mm Hg.

The overhead sight glass is observed for foaming and air is bled into the pump when necessary to minimize foaming.

To maximize the amount of final product produced, after stripping water for ~2 hours, 69.2 kgs of additional Sorbitol Solution #177010 is added to the reactor. The water removal process is continued for approximately 2 more hours.

The pressure is gradually reduced to obtain a vacuum of ~113 mmHg while maintaining the temperature at 130° C.

A total of 273.7 kgs of Sorbitol Solution #177010 is charged to the reactor. A total of 73.8 kgs (~90% of total) water is removed over a period of ~6 hours.

Co-Dehydration of Sugar Alcohol (Sorbitol) and Polyol (Glycerol)

Nitrogen is introduced into the reactor to reduce the vacuum and then 21.3 Kg of Glycerin is added to the reactor.

1.23 kilograms of 25 w % Sulfuric Acid is added subsurface into the reactor.

The reactor temperature is gradually increased to ~160° C.

The vacuum pump is re-started, the temperature and pressure are gradually re-established at 160° C. and a vacuum of ~113 mm Hg and maintained for ~3 hours.

Approximately 41.2 Kgs additional water is collected in the overhead receiver.

The reaction is stopped by introducing 0.80 Kgs of 88 w % Aqueous Potassium Hydroxide subsurface into the reactor.

An approximate flowrate of 25 cc/minute of Nitrogen is introduced to the reactor, subsurface, through the sparge ring.

After approximately 30 minutes, the Nitrogen, the hot oil heater and the vacuum pump are stopped.

The reactor is pressured up to approximately 20 kpa with Nitrogen and the overhead valved closed.

The reactor is allowed to cool overnight gradually reaching ~75° C. after about 10 hours.

The final product is then unloaded from the reactor, through a 50 micron filter, into a drum. The total weight of the product is 171 kgs. The total overheads (water) collected during the co-dehydration process is 45.5 kgs. The properties of the reaction product (Sample 2-1) are set forth in Table 1.

If the reaction is catalyzed with an acid, the acid value of the reaction product may be lowered further by the addition of a base to the reaction product. Typically when the catalyst is neutralized, greater than a stoichiometric amount of neutralization agent is added to reduce the acid value to the desired level. Typically bases such potassium hydroxide and sodium hydroxide are utilized. The use of such a base may lower the acid value of the reaction product below that obtained from the acid catalyzed reaction, for example less than 2 mg KOH/gram, preferably less than 1.5 mg KOH/gram, more preferably less than 1.0 mg KOH/gram, and in some instances less than 0.5 mg KOH/gram. Referring to Table 1, if KOH is added to the reaction products of Samples 1-1 to 2-1, an acid value (AV) less than 1.5, 1.0 or 05 mg KOH/gram or less can readily be obtained.

Description of Seeding Tests:

In order to determine the potential for crystallization during storage, shipping, and/or handling, Samples 1-1 to 1-4 and 2-1 are seeded with isosorbide crystals at least 99% pure at 25° C. as follows:

Procedure:

10-20 grams of each Sample to be tested is placed in a 20-50 ml clear, colorless, glass bottle, and a very small amount of finely ground isosorbide (usually less that 0.1 wt %) is added to each glass bottle and blended with the Sample material. The seeded Samples are left at room temperature for at least 24 hours.

The results of the seeding of the samples for Examples 1 and 2 are set forth below in Table 2.

TABLE 2

| Sample No. | Results after seeding |
| --- | --- |
| 1-1 | Solid |
| 1-2 | Partially Solid |
| 1-3 | Liquid |
| 1-4 | Liquid |
| 2-1 | Liquid |

As can be seen from Table 2, the reaction products having less than 50% by weight isosorbide were either liquid or only partially solid even after seeding as described above. Additionally, even Sample 1-2, which was partially solid when the neat reaction product was seeded, remained liquid when only 5 percent by weight of a polyol (DEG) was added to the reaction product before seeding was carried out. Table 3 shows the viscosities for Samples 1-1 to 1-4 and 2-1 both as neat products (i.e. no diluent added) and with various quantities of diluents added. The viscosities for the Samples were measured prior to seeding. This example shows that liquid polyols of the invention can be obtained that exhibit relatively low values for viscosity as set forth in Table 3.

TABLE 3

| | Sample No. | | | | |
| --- | --- | --- | --- | --- | --- |
| | 1-1 | 1-2 | 1-3 | 1-4 | 2-1 |
| Water Content of neat Samples (wt %) | 0.82% | 0.69% | 0.94% | 0.71% | 1.23% |
| Viscosity @25° C. of Neat Samples (Pa · s) | 18 | 26 | 37 | 57 | 23 |
| Viscosity @25° C. of Neat Samples + 5 wt % DEG with 1 wt % Water) (Pa · s) | 8.7 | 13 | 18 | 30 | 12 |
| Seeding Results of Neat Samples with 5 wt % DEG + 1 wt % water | Full solid | Liquid | Liquid | Liquid | Liquid |
| Viscosity @25° C. of Neat Samples + 10 wt % DEG with 1 wt % Water (Pa · s) | 5 | 6.4 | 9.7 | 13 | — |

TABLE 3-continued

| | Sample No. | | | | |
|---|---|---|---|---|---|
| | 1-1 | 1-2 | 1-3 | 1-4 | 2-1 |
| Seeding Results of neat Samples (no diluent polyol added) | Partial solid | Liquid | Liquid | Liquid | — |

As discussed above, for purposes of this invention the isosorbide content is measured by high performance liquid chromatography (HPLC). Gel permeation chromatography (GPC) is not as accurate for determining isosorbide content as HPLC. However, the inventors have found that the isosorbide content can be estimated using the results obtained using GPC and adjusting the results using correlations developed that relate the results from GPC to the results from HPLC. The inventors have determined that the isosorbide content estimated from GPC is about 10-15% higher than the isosorbide content determined by the HPLC employed. Therefore, for purposes of estimating the isosorbide content of a reaction product, the estimate obtained by GPC can be reduced by about 12% to obtain an estimate of the true isosorbide content in the reaction product. This estimate should not be utilized to determine the true isosorbide content of the reaction product, but can be useful for instance where a rough estimate of the isosorbide content is desired, without the need for a lengthy and complex analysis. For example, when one of skill in the art is attempting to estimate the extent of reaction within the reactor, a sample can be obtained from the reaction vessel and analyzed using GPC to obtain an estimate of the isosorbide content of the reaction mixture. For example, if the sample indicated that the reactor contains 52 percent isosorbide, using the correction factor it can be estimated that the amount of isosorbide in the reaction mixture by HPLC would be about 40 percent by weight. This information can then be utilized to determine how much longer to continue the co-dehydration reaction.

Example 3

Co-Dehydration of Sorbitol with Various Polyols

Various co-dehydration reactions were carried out using different polyols, differing reaction temperatures, different catalysts and differing ratios of reactants to one another. The reactions were carried out using a process similar to the process described in Example 1, the reaction temperature, reactants and reactant weight percentages, and catalysts utilized are indicated in Table 4. The neat reaction products were blended with five and ten percent by weight diethylene glycol (DEG) and sufficient water was added so that the blends contained 1 percent by weight water. The viscosities were all measured prior to any seeding of the Samples. Seeding (as described above for Table 2) was carried out on the Samples incorporating 5 percent by weight DEG.

| | Recipe (i.e. sugar alcohol and reactant polyol weight percentages) | | | | | Properties of Neat samples | | | | |
|---|---|---|---|---|---|---|---|---|---|---|
| Sample No. | SBT [%] | GLY [%] | DEG [%] | ERT [%] | Catalyst Type | Cat ppm | RX Temp, C. | OH# mg KOH/g | AV mg KG/g | Visc Pa · s |
| 3-1 | 90 | | 10 | | PTA | 5000 | 135 | 752 | 1.83 | 38.8 |
| 3-2 | 80 | | 20 | | PTA | 5000 | 135 | 794 | 2.13 | 22.6 |
| 3-3 | 70 | | 30 | | PTA | 5000 | 135 | 784 | 2.16 | 11.4 |
| 3-4 | 90 | 10 | | | PTA | 5000 | 135 | 983 | 1.95 | 41.6 |
| 3-5 | 80 | 20 | | | PTA | 5000 | 135 | 1015 | 1.96 | 20.8 |
| 3-6 | 90 | | | 10 | PTA | 5000 | 135 | 714 | 1.72 | 45.2 |
| 3-7 | 80 | | | 20 | PTA | 5000 | 135 | 746 | 1.91 | 38.2 |
| 3-8 | 70 | | | 30 | PTA | 5000 | 135 | 848 | 1.73 | 24.8 |
| 3-9 | 60 | | | 40 | PTA | 5000 | 135 | 693 | 1.96 | 16.2 |
| 3-10 | 50 | | | 50 | PTA | 5000 | 135 | 795 | 1.86 | 8.38 |
| 3-11 | 90 | 10 | | | SFA | 1400 | 135 | 990 | 1.15 | 56 |
| 3-12 | 80 | 20 | | | SFA | 1400 | 135 | 1014 | 1.19 | 28 |
| 3-13 | 90 | | | 10 | SFA | 1400 | 135 | 883 | 1.19 | 62.1 |
| 3-14 | 80 | | | 20 | SFA | 1400 | 135 | 880 | 1.48 | 41.1 |
| 3-15 | 80 | 10 | | 10 | SFA | 1400 | 135 | 918 | 1.19 | 33.2 |
| 3-16 | 70 | 20 | | 10 | SFA | 1400 | 135 | 954 | 1.05 | 25.7 |
| 3-17 | 70 | 10 | | 20 | SFA | 1400 | 135 | 966 | 1.25 | 27.3 |
| 3-18 | 60 | 20 | | 20 | SFA | 1400 | 135 | 1115 | 1 | 14 |
| 3-19 | 95 | 5 | | | SFA | 1400 | 135 | 871 | 1.34 | 42 |
| 3-20 | 95 | | 5 | | SFA | 1400 | 135 | 858 | 1.44 | 50.9 |
| 3-21 | 90 | 5 | 5 | | SFA | 1400 | 135 | 914 | 1.29 | 49 |
| 3-22 | 80 | 10 | 10 | | SFA | 1400 | 135 | 1095 | 1.26 | 32 |
| 3-23 | 90 | 10 | | | SFA | 1400 | 180 | 900 | 2.21 | 15 |
| 3-24 | 80 | 20 | | | SFA | 1400 | 180 | 895 | 1.47 | 13 |

| | Properties of Neat samples | | 5 wt % DEG with 1 wt % H2O | | | 10 wt % DEG with 1 wt % H2O | | | Seeding Results for Neat Reaction Product + 5 |
|---|---|---|---|---|---|---|---|---|---|
| Sample No. | H2O wt % | *ISB % wt % | Visc Pa · s | OH# Mg KOH/g | H2O wt % | Visc Pa · s | OH# mg KOH/g | H2O wt % | wt % DEG with 1 wt % H2O |
| 3-1 | 0.53 | 52 | 16.27 | 760 | 1.4 | 10 | 775 | 1.35 | L |
| 3-2 | 0.45 | 45 | 9.688 | 799 | 1.2 | 6.1 | 813 | 1.36 | L |
| 3-3 | 0.58 | 42 | 5.83 | 790 | 0.8 | 3.4 | 804 | 1.42 | L |
| 3-4 | 0.83 | 57 | 19.77 | 977 | 0.6 | 9.9 | 981 | 1.22 | L |
| 3-5 | 0.44 | 60 | 8.552 | 1006 | 1.1 | 5.5 | 1008 | 1.59 | L |
| 3-6 | 0.94 | 61 | 17.35 | 724 | 0.7 | 9.4 | 741 | 1.24 | P-S |
| 3-7 | 0.82 | 61 | 16.62 | 754 | 0.9 | 8.6 | 770 | 1.14 | L |

-continued

| | | | | | | | | | |
|---|---|---|---|---|---|---|---|---|---|
| 3-8 | 0.60 | 58 | 10.89 | 850 | 1 | 5.7 | 861 | 1.47 | L |
| 3-9 | 0.82 | 53 | 7.985 | 704 | 0.8 | 4.8 | 723 | 1.18 | L |
| 3-10 | 0.66 | 56 | 4.281 | 800 | 1 | 2.9 | 813 | 1.46 | L |
| 3-11 | 0.46 | 51 | 25/19 | 984 | 1.1 | 8/12 | 987 | 1.32 | L |
| 3-12 | 0.33 | 55 | 17/11 | 1006 | 1.4 | 7/8.1 | 1008 | 1.2 | L |
| 3-13 | 0.63 | 53 | 35.39 | 883 | 1.2 | 11 | 892 | 1.78 | L |
| 3-14 | 0.67 | 53 | 28.44 | 880 | 1 | 9.7 | 889 | 0.93 | L |
| 3-15 | 0.69 | 55 | 12.48 | 916 | 0.9 | 8.7 | 923 | 1.01 | L |
| 3-16 | 0.47 | 51 | 7.501 | 950 | 1 | 7 | 955 | 1 | L |
| 3-17 | 0.49 | 50 | 10.16 | 961 | 1.1 | 7.5 | 966 | 1.23 | L |
| 3-18 | 0.27 | 50 | 6.678 | 1101 | 1.2 | 4.6 | 1098 | 0.89 | L |
| 3-19 | 0.67 | 60 | 16.34 | 872 | 0.8 | 8.6 | 881 | 0.7 | P-S |
| 3-20 | 1.24 | 55 | 31 | 860 | 0.9 | 13 | 870 | 0.8 | L** |
| 3-21 | 0.74 | 53 | 22/20 | 912 | 1.1 | 11/12 | 919 | 0.97 | L |
| 3-22 | 0.53 | 51 | 9.5/11 | 1082 | 1.7 | 7.4/6.6 | 1081 | 1.12 | L |
| 3-23 | 1.42 | 68 | 8.6 | 899 | 1.3 | 5.8 | 907 | 1.27 | S |
| 3-24 | 1 | 68 | 7.8 | 894 | 0.8 | 4.8 | 903 | 0.76 | L** |

*The estimated isosorbide content (wt %) is determined by measuring the isosorbide content by GPC and subtracting 12.
**Samples 3-20 and 3-24 exhibit rough surfaces after seeding. This may indicate that eventually substantial crystals may develop.

Example 4

The reaction products of Samples 1-1 to 1-4 together with Samples 1-5 to 1-7 (as described below) were mixed together in the ratios indicated in Table 5. As can be seen from Table 5, a liquid containing the blends of reaction products together with 5 percent by weight DEG with less than or equal to 1 percent by weight water overall remained a liquid after seeding as described above, even though the liquids containing the individual reaction products with 5 percent by weight DEG with less than or equal to 1 percent by weight water may have Sample 1-7 is the reaction product made according to the procedure of Example 1, wherein the isosorbide is approximately 19.39 percent by weight as estimated by subtracting 12 from the isosorbide content indicated by GPC. The AV number is 1.15 mg KOH/gram and OH# is 1064 mg KOH/gram. Sample 1-7 when combined with 5 percent by weight DEG with less than or equal to 1 percent by weight water had a viscosity before seeding of 56 Pa·s at 25° C. and remained a liquid after seeding.

TABLE 5

| Sample No. ID | 1-5 (wt %) | 1-1 (wt %) | 1-2 (wt %) | 1-3 (wt %) | 1-4 (wt %) | 1-6 (wt %) | 1-7 (wt %) | *ISB (wt %) | H2O (wt %) | 25 C. Viscosity-Neat (Pa·s) | 25 C. Viscosity Neat + 5 wt % DEG with ≤1 wt % water (Pa·s) | Seeding Results For Neat Reaction Product + 5 wt % DEG with ≤1 wt % H2O |
|---|---|---|---|---|---|---|---|---|---|---|---|---|
| 4-1 | 55 | | | | | 45 | | 47.3 | 0.78 | 26.9 | 13.5 | Liquid |
| 4-2 | | 52 | | | 48 | | | 44.17 | 0.73 | 29.4 | 12.9 | Liquid |
| 4-3 | | | 45 | 55 | | | | 43.02 | 0.84 | 29 | 13.2 | Liquid |
| 4-4 | 75 | | | | | | 25 | 45.36 | 0.69 | 30.98 | 13.3 | Liquid |

*The estimated isosorbide content (wt %) was determined by measuring the isosorbide content by GPC and subtracting 12.
** All the samples of Table 5 had less than 1 percent by weight water.

formed a solid or partially solidified liquid upon similar seeding. This shows that a blend of two reaction products having the desired level of isosorbide may remain as a liquid after seeding even though one of the individual component reaction products would not have similar properties.

Sample 1-5 is the reaction product made according to the procedure of Example 1, wherein the isosorbide is approximately 57.3 percent by weight as estimated by measuring by GPC. The AV number is 1.88 mg KOH/gram and OH# is 904 mg KOH/gram. Sample 1-5 when combined with 5 percent by weight DEG with less than or equal to 1 percent by weight water had a viscosity before seeding of 7 Pa·s at 25° C. and formed a solid upon seeding.

Sample 1-6 is the reaction product made according to the procedure of Example 1, wherein the isosorbide is approximately 26.1 percent by weight as estimated subtracting 12 from the isosorbide content indicated by GPC. The AV number is 1.35 mg KOH/gram and OH# is 1021 mg KOH/gram. Sample 1-6 when combined with 5 percent by weight DEG with less than or equal to 1 percent by weight water had a viscosity before seeding of 44 Pa·s at 25° C. and remained a liquid after seeding.

Example 5

Commercial Bunstock Foam Trial

A commercial Bunstock rigid isocyanurate foam line was used to evaluate the performance of the inventive polyol. A foam formulation was developed to run on the line (see Table 6 below). Three runs were made, starting with a Control run (Run #1) without any inventive polyol followed by the trial runs (Runs #2 and #3) where approximately 15% of TER-ATE-4020 was replaced with Sample 5-1, which is a solution containing: 95 percent by weight of the reaction product of Sample 2-1 and 5 percent by weight diethylene glycol (DEG). Sample 5-1 contained 1 percent by weight water. The formulations containing Sample 5-1 react slower than the Control and therefore require higher levels of catalysts as set forth in Table 6. The isocyanate index was fixed at 250 in Runs #1 and #2 and lowered to 180 in Run #3. A target of 32 kg/m³ for density of the foams was attempted for all runs.

Prior to each run, a blend of polyol, fire retardant, surfactant and water was weighed into an agitated run tank according to the formulations in Table 6, below. The blend was circulated through the low pressure mix head and back to the run tank. During each run catalysts flows were individually metered directly into the mix head. The n-Pentane was metered into the run tank line, through a static mixer, located just prior to the mix head. "Mondur E-489" was metered directly into the mix head. A total flow rate of about 91 kg per minute was run with a line speed of about 3 meters/minute.

TABLE 6

| | RUN | | |
|---|---|---|---|
| | #1 parts | #2 parts | #3 parts |
| Sample 5-1 | 0 | 14.5 | 15.4 |
| TERATE-4020 | 77.2 | 58 | 61.9 |
| DC-197 | 1.5 | 1.7 | 1.8 |
| AB-TMCP | 3.9 | 2.9 | 3.1 |
| POLYCAT-5 | 0.15 | 0.8 | 0.7 |
| TMR-3 | 1.8 | 3.1 | 2.6 |
| TR-52 | 1.2 | 1.6 | 1.3 |
| n-Pentane | 13.9 | 17 | 13.2 |
| WATER | 0.4 | 0.4 | 0.5 |
| Isocyanate Index | 250 | 250 | 180 |
| A:B RATIO (by weight) | 63:37 | 69:31 | 62:38 |
| LINESPEED (m/min) | 3.1 | 3.1 | 3.1 |
| TOTAL FLOW (kg/min) | 91 | 91 | 91 |
| BUN DENSITY (kg/m$^3$) | 29.9 | 28.6 | 28.2 |

As can be seen in Tables 7 and 8 below, the inventive foams provided compressive strength comparable to the control foam formulations, even when the isocyanate index was reduced to 180. This will allow less polyisocyanate to be used in the manufacture of the foam, and still provide adequate compressive strength. Additionally, as can be seen from Table 8, the inventive foams had either equivalent or lower k-Factor compared to the control foam. The lower k-Factor will enhance the insulation capacity of the rigid polyisocyanurate foams. Also, as can be seen in Table 8, the other physical properties of the polyisocyanurate inventive foam (Run#3) are comparable to the properties of the polyisocyanurate control foam (Run#1).

Surprisingly for polyisocyanurate foams equivalent physical properties to typical PIR foams can be achieved with the use of a lower isocyanate index; or improved physical properties can be obtained at a similar isocyanate index. This will reduce the cost of manufacturing the foams. For example, a foam can be manufactured typically using from 10 to 40 (sometimes 15 to 25) percent by weight of the inventive polyol in the polyol formulation with a isocyanate index typically from 150 to 300 (for example 180 to 260); and obtain a FIR foam having compressive strength in the Y Direction of at least 150 (preferably at least 180) kilopascals, an initial k-Factor of less than 0.027 (preferably less than 0.026). Preferably, the compressive strength in the X Direction is at least 100 (preferably at least 120) kilopascals, and the compressive strength in the Z Direction is at least 100 (preferably at least 120) kilopascals.

Bunstock Rigid Polyisocyanurate Foam Properties

TABLE 7

Three-Dimensional Compressive Strength (kPa)

| | Control Foam (Run #1) | Inventive Foam (Run #2) | Inventive Foam (Run #3) |
|---|---|---|---|
| X Direction | 117.4 | 106.7 | 103.8 |
| Y Direction | 150.4 | 192.5 | 180.5 |
| Z Direction | 199.6 | 114.3 | 166.7 |

X Direction = Across the Conveyor, Y Direction = Vertical Direction, and Z Direction = Down the Conveyor

TABLE 8

Other Properties of the Polyisocyanurate Foams

| | Control Foam (Run #1) | Inventive Foam (Run #2) | Inventive Foam (Run #3) |
|---|---|---|---|
| Density (kg/m$^3$) | 31.2 | 29.0 | 27.5 |
| % Closed Cells | 78.5 | 83.9 | 84.2 |
| k-Factor(W/m × K) Day 1 | 0.0262 | 0.0262 | 0.0256 |
| k-Factor (W/m × K) Day 11 | 0.0275 | 0.0265 | 0.0262 |
| k-Factor (W/m × K) Day 28 | 0.0284 | 0.0269 | 0.0265 |

We claim:

1. A composition comprising the reaction product of the co-dehydration of a sugar alcohol and a reactant polyol having a number average hydroxyl functionality less than 4.0, wherein the composition exhibits a viscosity of from about 4 to about 40 Pa-s at 25° C.

2. The composition of claim 1, wherein the sugar alcohol comprises mannitol, sorbitol, xylitol, erythritol, or mixtures thereof.

3. The composition of claim 1, wherein the sugar alcohol comprises sorbitol and the reactant polyol has a number average hydroxyl functionality of from 2.0 to 3.0.

4. The composition of claim 1, wherein the reaction product comprises from about 25 to about 65 weight percent isosorbide, and at least 2 percent oligomers.

5. The composition of claim 1, wherein the sugar alcohol comprises sorbitol.

6. The composition of claim 1, wherein the reactant polyol has an average molecular weight of from about 50 to about 300 Daltons.

7. The composition of claim 1, wherein the reactant polyol has a molecular weight of from about 60 to about 200 Daltons.

8. The composition of claim 1, wherein the reactant polyol is selected from the group consisting of glycols, ethylene glycol, diethylene glycol, dipropylene glycol, propylene glycol, polyethylene glycol, 1,3 propanediol, poly(1,3-propanediol), 1,4-butanediol, poly(1,4-butanediol), polypropylene glycol, glycerol, glycerol ethers, 1,4-dihydroxycyclohexane and mixtures thereof.

9. The composition of claim 1, wherein the reactant polyol has a number average hydroxyl functionality (Fn) of from about 2 to about 3.

10. The composition of claim 9, wherein the reactant polyol comprises glycerol.

11. The composition of claim 10, wherein the reaction product has at least about 3 percent by weight oligomers.

12. The composition of claim 11, wherein the reaction product has at least about 5 percent by weight oligomers.

13. The composition of claim 1, wherein the reaction product has from about 30 to about 58 percent by weight isosorbide.

14. The composition of claim 13, wherein the reaction product has from about 35 to about 50 percent by weight isosorbide.

15. The composition of claim 1, wherein a weight ratio of reactant polyol to sugar alcohol is from about 1:99 to about 40:60.

16. The composition of claim 1, wherein the composition is liquid at room temperature.

17. A composition comprising the reaction product of the co-dehydration of a sugar alcohol and a reactant polyol having a number average hydroxyl functionality less than 4.0, wherein the composition is liquid at room temperature and remains liquid for at least 8 hours after seed crystals are introduced into the composition, wherein the reactant polyol is selected from the group consisting of ethylene glycol, diethylene glycol, dipropylene glycol, propylene glycol, polyethylene glycol, 1,3 propanediol, poly(1,3-propanediol), 1,4-butanediol, poly(1,4-butanediol), polypropylene glycol, glycerol, glycerol ethers, 1,4-dihydroxycyclohexane and mixtures thereof.

18. A rigid foam made from the reaction of the composition of claim 1 with a polyisocyanate.

19. A process for the production of a liquid polyol composition of claim 1 that will remain a liquid at room temperature, the process comprising:

(a) reacting sorbitol with a reactant polyol having an number average functionality (Fri) of from two to three with from about 0.01 percent by weight to about 5 percent by weight acid at a temperature of from about 100 C to 195 C;

(b) removing water from the reaction mixture;

(c) continuing the reaction to obtain a liquid polyol comprising from about 25 to about 65 percent by weight isosorbide, at least 2 percent by weight oligomers, and having a viscosity of less than about 60 Pa·s at 25 C and a hydroxyl number of from about 500 to about 1200 mg KOH/gram polyol.

20. The process of claim 19, wherein the liquid polyol has a viscosity of less than 30 Pa·s at 25 C.

21. The process of claim 19, wherein the reactant polyol comprises glycerol and the liquid polyol formed comprises from about 35 to 50 percent by weight isosorbide and less than 8 percent by weight free glycerol and wherein the liquid polyol formed is a liquid at 25 C, has a viscosity at 25 C of less than 30 Pa-s, has a hydroxyl number of from about 800 to 1100 mg KOH/gram.

22. The process of claim 19, further comprising:

(d) stopping the reaction of step (a); and (e) after step (d) adding a diluent having at least two hydroxyl groups to the liquid polyol wherein sufficient diluent is added in step (e) to result in a weight ratio of diluent added to liquid polyol of from 1:99 to 2:8.

* * * * *